US005698431A

United States Patent [19]
Leib

[11] Patent Number: 5,698,431
[45] Date of Patent: Dec. 16, 1997

[54] HERPES SIMPLEX VIRUS MUTANT UL41NHB

[75] Inventor: David A. Leib, St. Louis, Mo.

[73] Assignee: Washington University, St. Louis, Mo.

[21] Appl. No.: 385,942

[22] Filed: Feb. 9, 1995

[51] Int. Cl.$^6$ .................. C12N 7/04; C12N 7/01
[52] U.S. Cl. .................. 435/236; 435/235.1; 435/948
[58] Field of Search ................... 435/235.1, 236

[56] References Cited

FOREIGN PATENT DOCUMENTS

WO 95/13391  5/1995  WIPO .

OTHER PUBLICATIONS

Fenwick et al., J. Gen. Virol. 71:2961–2967 (1990).
Levatte et al; Gene Therapy, vol. 1, Supp. 1, 1993, p. S77.
Becker et al; Virus Genes, vol. 7, No. 2, 1993, pp. 133–143.
Strelow et al; J. Virol vol. 69, No. 11, 1995, pp. 6779–6786.
Berthomme, H.B. et al, 1993 Virology 193: 1028–1032.
Kwong, A.D. et al, 1987 Proc. Natl. Acad. Sci. USA 84 1926–1930.
Kwong, A.D. et al, 1989 J. Virol. 63: 4834–4839.
Leib, D.A. et al, 1989 J. Virol. 63: 759–768.
Leib, D.A. et al, 1991 Proc. Natl. Acad. Sci. USA 88: 48–52.
McGeoch, D.J. et al, 1988 J. Gen. Virol. 69: 1531–1574.
Rader, K.A. et al., 1993 J. Gen. Virol. 74: 1859–1869.
Read, G.S. et al, 1993 J. Virol. 67: 7149–7160.
Smibert, C.A. et al., 1992 J.Gen. Virol. 73: 467–470.

*Primary Examiner*—George C. Elliott
*Assistant Examiner*—Johnny F. Railey, II
*Attorney, Agent, or Firm*—Scott J. Meyer

[57] ABSTRACT

A herpes simplex virus (HSV) mutant, UL41NHB, is disclosed which is deficient in the virion host shutoff (vhs) function. This mutant is shown to be profoundly attenuated in its ability to replicate at the periphery and in the nervous system, and in its ability to reactivate from latency.

1 Claim, 8 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
 ( A ) LENGTH: 28 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc ="synthetic DNA"

( x i ) SEQUENCE DESCRIPTION: SEQ ID NO:1:

GGGCTGGGCC TCGATCAGAA GGACTTGG 28

HERPES SIMPLEX VIRUS MUTANT UL41NHB

ACKNOWLEDGEMENT OF GOVERNMENT SUPPORT

This work was supported in part by Public Health Service Grant RO1 EY10707. The Government has certain rights in the invention.

BACKGROUND OF THE INVENTION

This invention relates to herpes simplex virus (HSV) mutants and, more particularly, to HSV mutants deficient in the virion host shutoff (vhs) function. Mutation of vhs results in a virus which is profoundly attenuated in its ability to replicate at the periphery and in the nervous system, and in its ability to reactivate from latency. These mutants thus are also useful for the development of HSV vaccines, as well as establishing the vhs as an antiviral target.

(Note: Literature references on the following background information and on conventional test methods and laboratory procedures well known to the ordinary person skilled in the art, and other such state-of-the-art techniques as used herein, are indicated in parentheses, and appended at the end of the specification.)

Viral gene regulation during infection by herpes simplex virus type 1 (HSV-1) requires the coordinate regulation of all three temporal classes of viral genes: immediate-early ($\alpha$), early ($\beta$), and late ($\gamma$) (31,32). This is accomplished in part through the action of a 58 kD phosphoprotein encoded by the viral UL41 gene which is known as the virion-associated host shutoff (vhs) protein (38, 39, 59, 65, 69, 75). Shutoff of macromolecular synthesis in HSV-infected cells is accomplished through two apparently independent mechanisms. Early shutoff occurs in the absence of viral gene expression and is due to the presence of approximately 200 copies of the vhs protein within the tegument of the infecting virus (38, 58, 65). Shutoff can therefore occur immediately upon viral infection, even though the UL41 gene itself is expressed late during infection (61). A secondary shutoff which requires viral gene expression occurs late during infection and appears to be dependent upon the presence of the immediate-early protein ICP27 (15, 54, 58).

Both host and viral RNAs are rapidly destabilized by an indeterminate mechanism in the presence of vhs (38, 55, 58, 75). All three temporal classes of viral messages and most cellular messages studied to date are destabilized by vhs with the exception of ribosomal RNAs (56). An additional exception to the observed degradation of cellular RNA has been seen in cultured neurons, where no significant shutoff of of protein synthesis is observed following infection with HSV-1 (50). Viruses containing mutations in the vhs function have therefore been isolated based on their inability to cause degradation of host mRNA concomitant with an over accumulation of immediate-early viral transcripts (38, 58, 75). Although vhs is not essential for virus growth, vhs⁻ mutants have slight but reproducible growth deficits in that they produce smaller plaques than wild-type, are rapidly outgrown by wild-type virus in mixed infections and have burst sizes which are reduced between two- to five-fold (40, 58).

Although a number of studies have addressed the role of vhs in lytic infections and in the cascade of viral gene expression, very little is known concerning the role of vhs in latency and pathogenesis. Recent sequence analysis (3) of the genomes of HSV-1, HSV-2, varicella-zoster virus (VZV), equine herpes virus type 1 (EHV-1) and pseudorabies virus (PRY) has revealed that each has a UL41 homolog.

The neurotropic nature of these five viruses, coupled with the apparent absence of homologs in either the sequenced $\beta$- or $\gamma$-herpes viruses, suggests to the present inventors a potentially important role for vhs in HSV-induced neuropathogenesis. In humans and in experimental animals the pathogenesis of HSV can occur in a series of discreet stages. Acute infection at peripheral sites involves viral replication and is followed by viral entry into neuronal terminae. Virus is transported by intra-axonal flow to sensory ganglia, where further acute viral replication may occur. This event is followed by the down regulation of viral gene expression and the establishment of latency in the neuronal nuclei.

Viral DNA remains episomal, and the only readily demonstrable viral gene products found during latency are the latency-associated transcripts (LATs) (25). The latent state may periodically break down in response to certain stimuli, leading to reactivation of virus and shedding of infectious virus at the periphery. The molecular mechanisms responsible for the altered regulation of viral gene expression during the establishment, maintenance and reactivation of latency remain poorly understood. The conservation of the UL41 gene in five of the neurotropic herpesviruses together with the inability of vhs to cause decreased protein synthesis in cultured neurons led to the present inventors' hypothesis that vhs may be important in this regulatory process.

BRIEF DESCRIPTION OF THE INVENTION

In accordance with the present invention, HSV mutants deficient in the vhs function are generated to produce a virus which is profoundly attenuated in its ability to replicate at the periphery and in the nervous system, and in its ability to reactivate from latency.

In order to illustrate the invention, the inventors generated a mutant virus, UL41NHB, which carries a nonsense linker inserted into the UL41 open reading frame. UL41NHB encodes a truncated form of vhs and fails to induce the degradation of glyceraldehyde-3-phosphate-dehydrogenase (GAPDH) mRNA.

The growth of UL41NHB was compared to wild-type KOS and to vhs-ΔSma, an in-frame UL41 deletion mutant (46), in Vero cells and in contact-inhibited $C_3H/10T\frac{1}{2}$ mouse cells.

The growth of the vhs mutants was not significantly reduced in Vero cells but was reduced by up to 100 fold in $C_3H/10T\frac{1}{2}$ cells, indicating a significant impairment of growth in contact-inhibited cells.

Consistent with this finding, following corneal inoculation or intracerebral injection of mice with KOS, UL41NHB or vhs-ΔSma, both vhs mutant viruses were impaired in their ability to grow in corneas, in trigeminal ganglia and in brains compared to KOS. Explant cocultivation studies revealed an impairment in the reactivation of UL41NHB (1/28, or 4%) and vhs-ΔSma (%0, or 0%) when compared to KOS (44/62, or 71%). The UL41 mutant viruses failed to reactivate despite the demonstrated presence of a low level of latent viral DNA in trigeminal ganglia. Taken together, these results show that vhs represents an important determinant of viral neuropathogenicity.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawings.

BRIEF DESCRIPTION OF THE DRAWINGS

(A) Prototypical arrangement of the HSV-1 genome, showing unique long ($U_L$) and unique short ($U_S$) segments flanked by internal (a', b', c') and terminal (a, b, c) repeats. UL41 is transcribed in a leftward direction, as indicated by the arrow.

(B) Expanded view of UL41 open reading frame (ORF) showing selected restriction enzyme sites. Numbering is as per McGeogh et al. (47).

(C) Wild-type UL41 ORF showing conserved domains I–IV. The domains are those defined by Berthomme et al. (1) and are conserved among HSV-1, HSV-2, VZV, PRV and EHV.

(D) pGAL-SCA was constructed by the insertion of an HCMV-β-gal cassette into the Sca I site of UL41.

(E) BGS41 was constructed by the recombination of wild-type KOS infectious DNA with pGAL-SCA.

(F) pUL41Hpa-Stop was constructed by the insertion of a nonsense linker (4) containing a unique Hpa I restriction site and stop codons in all three reading frames into the Nru I site of UL41 in domain III.

(G) UL41NHB resulted from the recombination of pUL41Hpa-Stop with infectious BGS41 DNA.

(H) vhs 1 has been shown to contain a substitution of Thr to Ils at amino acid 214 (marked by asterisk).

(I) vhs-ΔSma (46) is an in-frame deletion of UL41 between Sma I sites.

FIG. 2 shows the Southern blot analysis of recombinant viruses. Expected sizes resulting from a Hpa I digestion are: 13.8 kb, 2.9 kb and 624 bp for BGS41, and 11.2 kb and 1.8 kb for the recombinant virus. Lane 1: BGS41 infectious DNA, lanes 2–12: individual isolates from third round plaque purification showing the expected bands. The 624 bp band does not appear on this gel. The virus in lane 12 was amplified into a high titer stock and designated UL41NHB.

FIG. 3 shows the Western blot analysis of vhs (UL41) viral mutants. Viral lysates of each of the indicated viruses were prepared by boiling in SDS lysis buffer. Proteins were resolved by SDS-PAGE and analyzed by western blotting with an antiserum raised against a vhs-protein A fusion (57). The expected sizes of the vhs polypeptides are as follows: KOS (wild-type) 58-kDa, UL41NHB 26 kDa, vhs 1 58-kDa and vhs-ΔSma 31-kDa. Size markers (in kDa) are shown at the left.

FIG. 4, in two parts, A and B, shows the RNA degradation assay (RDA) by northern blot analysis probing for GAPDH. Vero cells in 100 mm tissue culture dishes were infected at an MOI of 209 and cytoplasmic RNA harveted at the times indicated.

FIG. 4A shows the autoradiographic image of northern blot probed for GAPDH. The film in FIG. 4A was reprobed for 28S ribosomal subunit and scanned using an imaging densitometer. GADPH amounts were first normalized to 28S signals at each time point and are shown relative to the GAPDH level expressed by mock-infected cells at four hours post-infection. The results of this analysis are shown in FIG. 4B. ■ mock; ▌ KOS; ▌vhs-ΔSma; □UL41NHB.

In FIG. 5A, subconfluent Vero cells were infected at an MOI of 10 pfu/cell for single-step kinetics and in FIG. 5B, confluent $C_3H10T½$ cells were infected at an MOI of 0.005 for multi-step kinetics, each in 35 mm tissue culture dishes. At the times indicated, duplicate cultures were harvested and stored at −80° C. until assayed for viral titer on Vero cells. ■KOS; •UL41NHB; ▲vhs1; Δ-vhs-ΔSma.

Mice were inoculated intracerebrally with either $1\times10^3$ pfu in FIG. 6A, or $1\times10^5$ pfu in FIG. 6B of either KOS, vhs-ΔSma, or UL41NHB. Three mice from each viral infection group were sacrificed at the times indicated and their brains removed and stored at −80° C. until assay. The brains were homogenized in cell culture medium and titered on Vero cells. Each bar represents the logarithmic mean of virus obtained from three brains. ■KOS; ▌vhs-ΔSma; □UL41NHB.

In FIG. 7A, eye swabs were taken at 3, 24, 48, 72, 96 and 120 hours post-infection and in FIG. 7B, trigeminal ganglia were removed and assayed directly for infectious virus at 24, 48, 72, 96 and 120 hours post-inoculation. No infectious mutant virus was found in trigeminal ganglia at all time points tested, with the exception of one ganglion infected with UL41NHB at 96 hrs post-infection. This ganglion represents one (1) out of 28 ganglia assayed. Southern blot analysis of virus from this ganglion confirmed the presence of UL41NHB. ■KOS; ▌vhs-ΔSma; □UL41NHB.

In order to illustrate the invention in further detail, the following specific laboratory examples were carried out with the results indicated. Although specific examples are thus illustrated, it will be understood that the invention is not limited to these specific examples or the details therein.

EXAMPLES

Materials and Methods

Cells and viruses. African green monkey kidney (Vero) cells were propagated as described previously (57). Murine $C_3H/10T½$ (ATCC CCL 226) were propagated in Dulbecco's MEM supplemented with 10% fetal calf serum and antibiotics (250U of penicillin per ml and 2501 µg of streptomycin per ml) in a 5% $CO_2$ humidified chamber at 37° C. Cell line 3—3 was derived from Vero cells and expresses a complementing level of ICP27 as described previously (46).

(a) Virus growth. Growth and assay of the KOS strain of HSV-1 was done as described previously (57). The vhs⁻ mutants vhs-ΔSma and vhs1 were kindly provided by G. S. Read (55, 59). Viral mutants BGS41, UL41NHB, vhs-ΔSma and vhs1 were propagated as described for KOS. The ICP27 deletion mutant 5d/1.2 was grown as previously described (46).

(b) Generation of viral mutants. The viral mutants used in these examples were constructed from the parental strain KOS. Methods for constructing recombinants were described previously (42, 57). The KOS EcoRI A fragment was digested with Hind III and Hpa I, and the 3595 bp fragment containing the entire UL41 open reading frame (ORF) as well as flanking sequence was cloned into pGEM5D3 (43) at the Hind III site to generate plasmid pUL41. The β-gal cassette from pHCMV-MPI-lacZ (kindly provided by P. Olivo) was isolated as a 3079 bp Hind III-Sma I fragment and ligated into pUL41 partially digested with Sca I.

Plasmids were screened for the correct insertion of the β-gal cassette into the UL41 ORF, and an appropriate plasmid was designated pGALSCA-11. PGALSCA-11 was cotransfected into Vero cells with infectious KOS DNA and the progeny screened by blue/white selection (26), followed by Southern blot analysis for an altered Sal I digestion pattern.

Virus demonstrating the correct digestion pattern was plaque purified three times and a high titer stock was prepared and designated BGS41. This virus was used for the subsequent selection of other viruses. pUL41HpaStop was constructed by the insertion of a nonsense linker (12) containing stop codons in all three reading frames as well as a unique Hpa I site into the Nru I site of pUL41. Hind III-linearized pUL41HpaStop was cotransfected into Veros with infectious BGS41 DNA and the progeny screened first by blue/white selection followed by Southern blot analysis for an altered Hpa I digestion pattern. Virus demonstrating the expected Hpa I digestion pattern was plaque purified three times and a high titer stock was prepared and designated UL41NHB.

Animal procedures.

(a) Acute viral replication. Four- to six-week old randomly bred CD-1 female mice (Charles River Breeding Laboratories, Inc., Kingston, N.Y.) were anesthetized with ketamine and xylazine, their corneas bilaterally scarified and $2\times10^6$ pfu of virus in a volume of 5 µl was added as previously described (57, 78). Eye swab material and trigeminal ganglia were assayed for virus as previously described (42).

(b) Intracerebral Inoculations. Intracerebral inoculations were performed essentially as previously described (5, 44). In brief, mice were inoculated intracerebrally with 1 µl of virus inoculum containing either $1\times10^3$, $10^5$, or $5\times10^5$ pfu. At the indicated times post-infection, three mice infected with each of the indicated viruses were sacrificed and their brains dissected out, weighed and stored at $-80°$ C. Individual brains were homogenized in 4 ml media, clarified at 5000×g for 5 min. and assayed for virus on Vero or 3—3 cells.

(c) Reactivation from latency. Reactivation from latency was studied as per Leib et al (42). Briefly, mice were sacrificed on day 28 post-infection and their trigeminal ganglia removed. Ganglia were cut into eight pieces and explanted into Vero cell monolayers. After five days in culture, explants were frozen, thawed, homogenized, sonicated and assayed for infectious virus on fresh Vero cell monolayers.

Western blot analysis. $1\times10^8$ pfu of virus stock was pelleted, resuspended in 2× sample buffer, boiled and separated on a 12% acrylamide gel by SDS-PAGE. The proteins were transferred to nitrocellulose (Schleicher and Schuell) by published standard protocols (28).

The filters were probed for UL41 polypeptides with a previously described polyclonal antisera prepared against a vhs-protein A fusion (70) (kindly supplied by J. Smiley) at a 1:1000 dilution vhs-primary antibody complexes were visualized with a horseradish peroxidase-conjugated secondary antibody (goat anti-rabbit; Amersham) and an ECL Western blotting detection kit (Amersham) according to the manufacturer's instructions.

Southern blot analysis. Southern blot analysis of viral DNA was performed essentially as previously described (57, 63). pUL41 was labeled with 32p by nick translation for use as a probe in plaque purification of both BGS41 and UL41NHB.

Northern blot analysis and mRNA degradation assay (RDA). Total cytoplasmic RNA was prepared from monolayer cultures of infected or mock-infected Vero cells at various times post-infection essentially as previously described (37, 56). Monolayer cultures of between $5\times10^5$ and $5\times10^6$ cells were infected at an MOI of 20 with the indicated viruses.

Mock infected plates received Vero cell lysate only. At various times post-infection, cells were harvested by being washed twice with ice-cold phosphate-buffered saline and scraped into 200 µl of resuspension buffer (10 mM Tris pH 7.9, 1.5 mM NaCl, 1.5 mM $MgCl_2$+RNAsin at 100 U/ml). Cells were disrupted via 10 passages through a 25 gauge needle and the nuclei pelleted by low speed centrifugation.

Individual supernatants were removed to fresh tubes and an equal volume of urea buffer (10 mM Tris, pH 7.9, 7M urea, 0.35M NaCl, 10 mM EDTA, 1% SDS) was added. Samples were extracted twice with phenol-chloroform (24:1) and twice with chloroform alone. 2.5 volumes of cold ethanol were added and the samples were precipitated overnight at $-80°$ C.

The RNA was pelleted, washed with 75% ethanol, dried, resuspended in DEPC-treated water and formaldehyde-containing loading dye added. The RNA thus obtained per 100 mm dish of cells was electrophoresed through a 1.2% agarose gel cast in 1× MOPS/1% formaldehyde (4). The RNAs were transferred to nitrocellulose membranes by capillary blotting. MOPS=(3-[N-Morpholino]propane-sulfonic acid)

Filters were baked for 2 hrs under vacuum at $80°$ C. pRGAPDH13 (obtained from W. Parks; 23) was digested with Pst I and a 1.3 kb rat glyceraldehyde-3-phosphate dehydrogenase (GAPDH) fragment isolated and labeled with $^{32}P$ by random priming with a random priming kit (Promega, Madison, Wis.).

The oligonucleotide GGGCTGGGCCTCGATCAGAAGGACTTGG, [SEQ ID NO:1], specific for 28S ribosomal subunit, was labeled with $^{32}P$ by T4 polynucleotide kinase. Hybridization solutions and conditions have been previously described (4). Filters were first probed for GAPDH, stripped and reprobed for 28S ribosomal subunit.

Autoradiographic films were scanned using a densitometer (Biorad model GS-670) and each GAPDH value was first normalized to 28S ribosomal subunit signal at each time point, and is shown relative to the GAPDH level expressed by mock-infected cells at 4 hrs p.i.

Viral replication kinetics. One-step and multistep replication kinetics experiments were performed at $370°$ C. on confluent Vero or $C_3H/10T½$ cells as described previously (5). For one-step tests, the MOI was 5 pfu/cell; for multistep tests the MOI was 0.005 pfu/cell.

RESULTS

Construction of a nonsense mutant of UL41.

The inventors determined to construct a mutant of UL41 which would be likely to be phenotypically vhs⁻ and to use this mutant to elucidate a role for vhs in neuropathogenesis. To this end a virus was constructed which has an ochre codon inserted into conserved domain III (3; FIG. 1). A parent virus, BGS41, was first constructed by the insertion of an HCMV β-gal cassette (obtained from P. Olivo) into the Sca I site of UL41. This blue parental virus was then cotransfected with pUL41HpaStop, a plasmid containing a nonsense linker (12) with stop codons in all three reading frames and a novel Hpa I site inserted into the Nru I site of UL41.

Progeny were screened by blue/white selection followed by plaque purification and Southern blot analysis.

The initial blue/white screening procedure greatly simplified plaque purification in that, of five (5) white progeny picked during the first round of plaque purification, two (2) were plaque-pure by the second round.

Figure 1A:
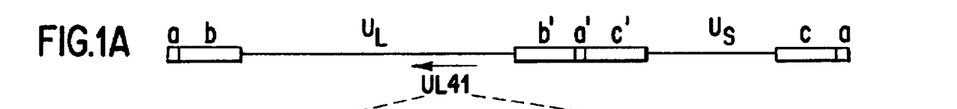
FIG. 1 (Parts A–I) shows the map of vhs (UL41) ORF and below which are shown the plasmids and viral mutants used in illustrative embodiments of the invention.
Figure 1B:
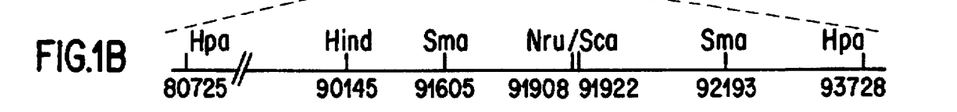
Figure 1C:
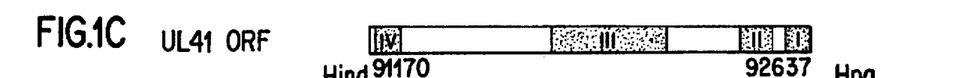
Figure 1D:
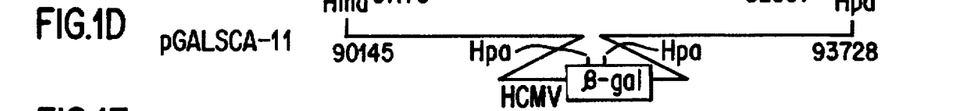
Figure 1E:
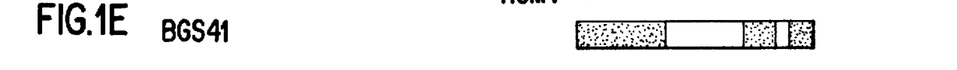
Figure 1F:
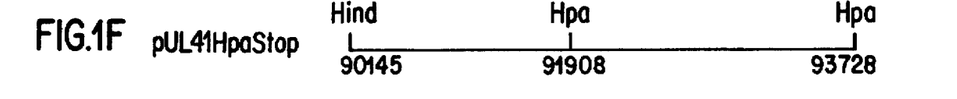
Figure 1G:
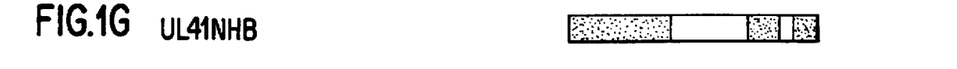
Figure 1H:
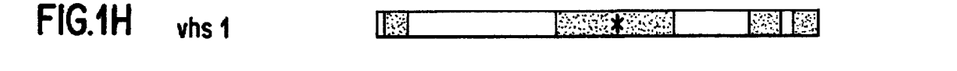
Figure 1I:
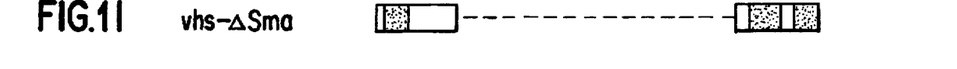
Figure 2:
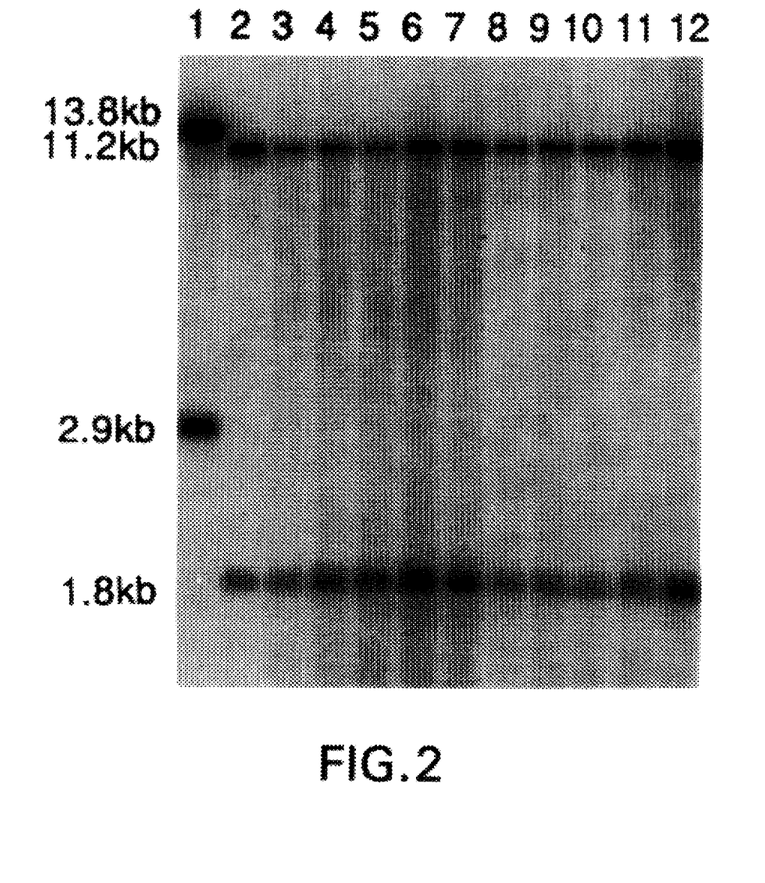

A third round of purification was performed and analyzed by restriction enzyme digest, as shown in FIG. 2. A map of parental virus and mutant plasmid is shown in FIG. 1.

The introduction of the stop linker into the Nru I site results in the destruction of this site as well as the generation of a novel Hpa I site which is present in the linker.

In addition, there are two Hpa I sites present in the β-gal cassette of BGS41 which are absent from pUL41HpaStop. Consequently, a Hpa I digestion of viral DNA, when probed with nick-translated pUL41, would be expected to yield 13.8 kb, 2.9 kb and 624 bp fragments for parental BGS41 versus 11.2 kb and 1.8 kb fragments for the recombinant progeny containing the mutation.

As can be seen from FIG. 2, third-round plaque purification yielded 11 isolates (lanes 2–12) showing the recombinant phenotype. The virus in lane 12 was subsequently amplified into a high titer stock and designated UL41NHB.

Figure 3:
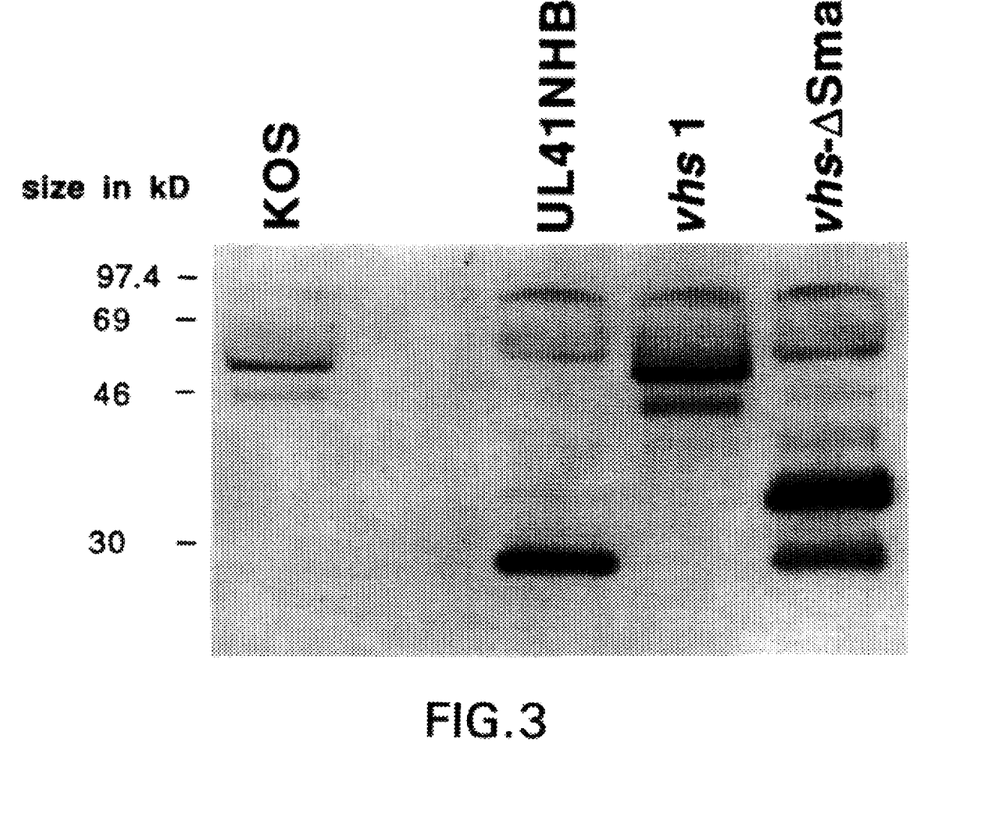

Detection of vhs polypeptides. Immunoblot analysis was performed to determine whether UL41NHB was actually a nonsense mutant of UL41, and whether this virus made a truncated vhs polypeptide of the expected size. A polyclonal antiserum raised against a vhs-protein A fusion (70) was used at a 1:1000 dilution to detect vhs polypeptides in viral preparations.

As shown in FIG. 3, this antiserum detected a protein with an apparent molecular might of 58 kD in KOS viral preparations, in agreement with previous published reports (59, 69).

In addition, proteins of 58 kD and 31 kD were detected for vital preparations of the vhs mutants vhs 1 and vhs-ΔSma, respectively, again in agreement with previously published results (59, 67).

A protein of approximately 28 kD was detected for UL41NHB, which is in close agreement with the predicted size of 26 kD. No vhs polypeptides were detected using extracts from mock-infected cells or when pre-immune sera were used.

These results demonstrate that the insertion of the stop linker into the UL41 open reading frame in the context of the UL41NHB virus resulted in a truncation at the appropriate site in the UL41 protein.

Effect of the UL41NHB mutation on the accumulation of GAPDH. It has been previously shown that the failure to degrade cellular messages is one of the characteristic properties' of vhs⁻ viruses (36, 38, 39, 40, 56, 65, 75).

The inventors determined to test UL41NHB for its inability to degrade glyceraldehyde-3-phosphate-dehydrogenase (GAPDH) mRNA in parallel with vhs-ΔSma, a vhs mutant previously shown to fail to degrade mRNA. GAPDH was chosen because it is a stable cellular message, and any effect seen would therefore not be due to inherent message instability.

Vero cells were mock-infected or infected at an MOI of 20 with either KOS, vhs-ΔSma or UL41NHB and cytoplasmic RNAs were harvested at 2, 4, 10 and 12 hours post-infection. The level of GAPDH mRNA was then analyzed by northern blotting with a GAPDH probe and an oligonucleotide specific for the 28S ribosomal subunit, and quantitated by densitometric scanning of autoradiographs.

28S was chosen as an internal control for loading since vhs does not degrade the ribosomal subunit RNAs. The level for mock-infected cells at four (4) hours post-infection was set to 100% and the normalized values were compared to this level.

Figure 4A:
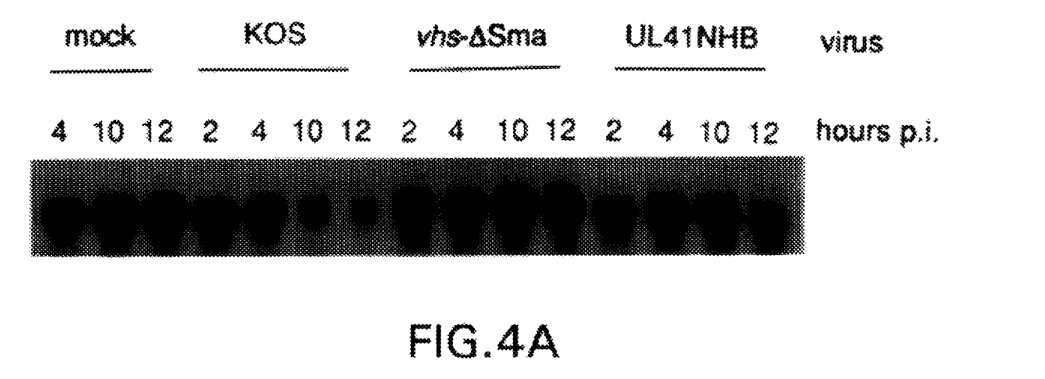
Figure 4B:
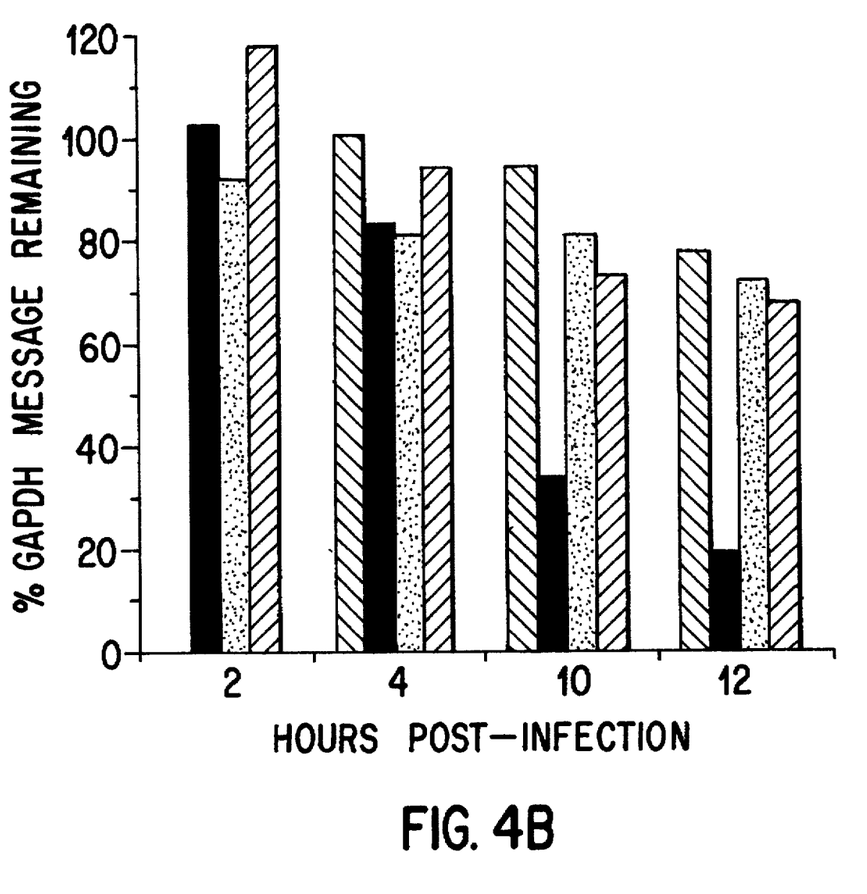

As can be seen in FIG. 4, infection with KOS leads to a decrease in the amount of GAPDH mRNA detectable over time. Infection with vhs-ΔSma serves as a vhs⁻ control. It can be seen from FIG. 4 that UL41NHB and vhs-ΔSma are indistinguishable both from each other and from mock-infected cells in that they cause no significant degradation of GAPDH mRNA at any time point tested.

Importantly, these results show that UL41NHB is behaving comparably to vhs-ΔSma in this assay, demonstrating that UL41NHB is phenotypically a vhs⁻ virus. Similar results were obtained when these tests were carried out under conditions of cycloheximide reversal and in the presence of actinomycin D alone.

Replication kinetics.

(a) In vitro. Having shown that UL41NHB is defective in vhs-induced shutoff function, the inventors then determined to examine the growth of this virus in vitro. Replication kinetics were examined in actively dividing Vero cells as well as in contact-inhibited mouse embryo cells ($C_3H/10T\frac{1}{2}$ cells). The vhs mutants vhs 1 and vhs-ΔSma were used as controls.

Figure 5A:
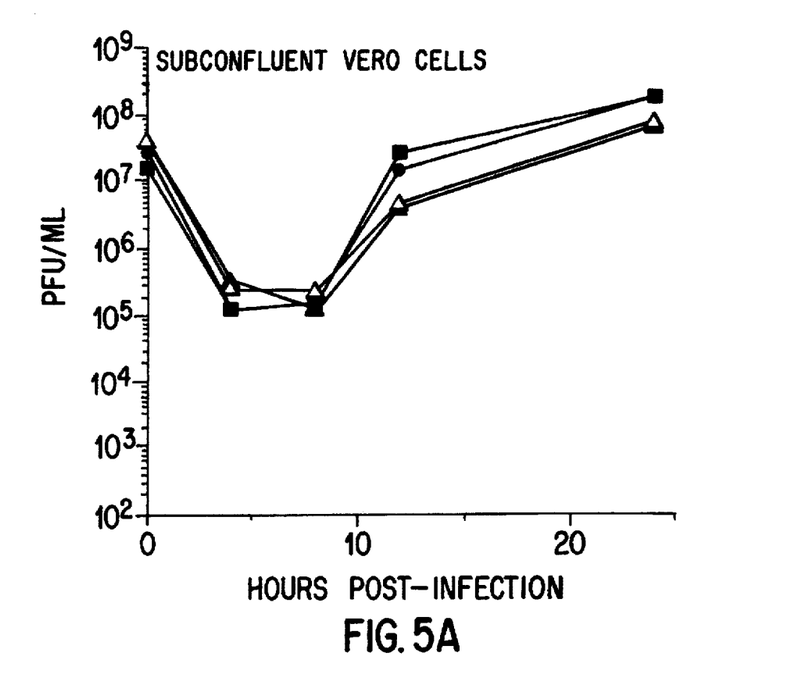
FIG. 5 in two parts, A and B, shows viral replication kinetics.

As shown in FIG. 5A, vhs 1, vhs-ΔSma and UL41NHB all replicated efficiently in Vero cells in a one-step growth curve. Viral yields and growth kinetics of the vhs mutants were not significantly decreased from those of KOS in these cells at the MOI tested.

These results are in agreement with Read et al (59), who have found that their mutant, vhs-ΔSma, had a marginal effect on virus growth in culture.

Figure 5B:
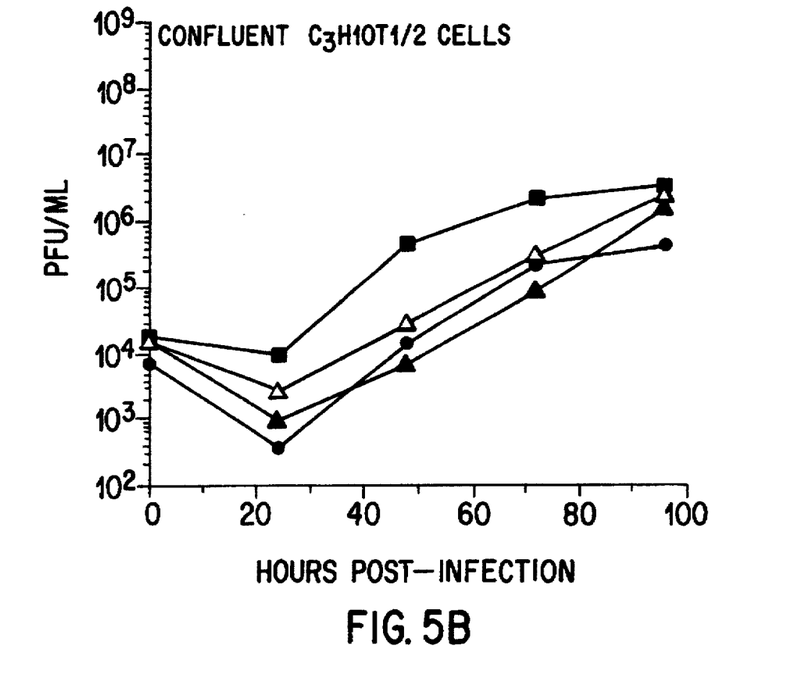

Multistep growth kinetics were next examined in contact-inhibited $C_3H/10T\frac{1}{2}$ cells. Confluent monolayers of these cells were infected at an MOI of 0.005 and vital replication assayed for four days. The results of this analysis are shown in FIG. 5B.

As can be seen, the replication of vhs 1, vhs-ΔSma and UL41NHB was restricted in these cells. The rate of viral replication appears to be comparable to that of KOS, but the yields of vhs⁻ viruses were reduced by 10- to 100-fold compared to levels of KOS at days one through three post-infection.

By four days post-infection the yield of vhs 1 and vhs-ΔSma approached that of KOS, while UL41NHB yields were still reduced by almost 10-fold. These results indicate that vhs mutants are restricted for replication in quiescent, non-neuronal cells, but less so in actively dividing fibroblasts.

(b) in vivo. Having demonstrated a restriction on replication in cell culture, the inventors then examined the growth of vhs mutants in mouse brains, corneas and trigeminal ganglia. Viral titer in mouse brains was examined following intracerebral inoculation with either $1 \times 10^3$ pfu or $1 \times 10^5$ pfu of wild-type and mutant viruses. The inventors chose an initial input inoculum of $1 \times 10^3$ pfu (FIG. 6b) in order to be below the $LD_{50}$ for KOS (13).

Figure 6A:
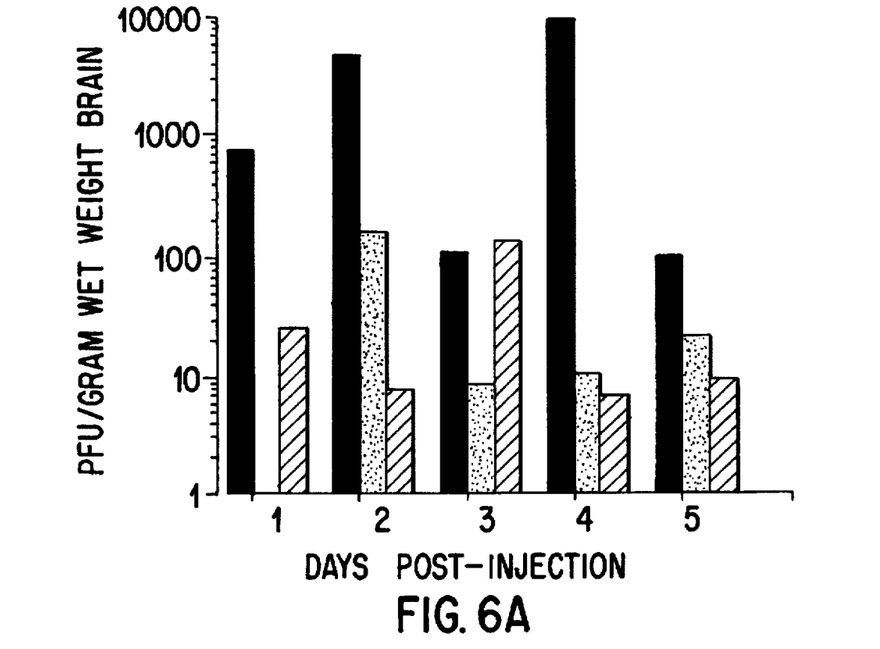
FIG. 6, in two parts, A and B, shows viral titers in mouse brains.
Figure 6B:
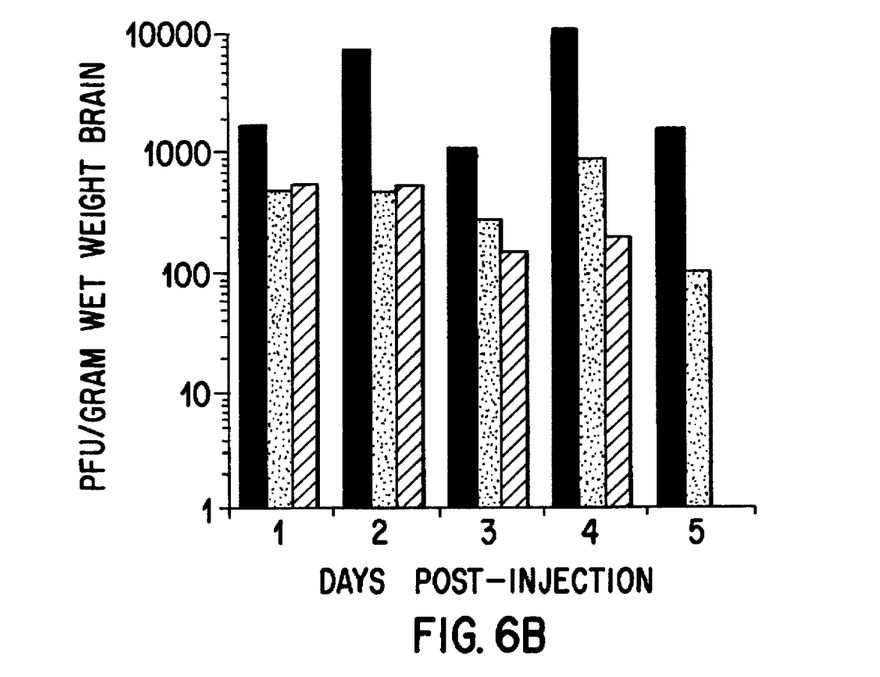

Since only one KOS-infected mouse died in the initial test and the levels of recoverable virus were low, the intracerebral inoculation was repeated with $1 \times 10^5$ pfu of mutant and wild-type virus (FIG. 6b).

Replication in the brain was assayed for five consecutive days. The results are shown in FIG. 6. Each bar represents the logarithmic mean of three brains per time point, graphed as pfu/gram wet weight brain versus days post infection.

These results show that the titer found in the brain for the vhs mutant viruses was 10- to 100-fold down from the titer of KOS in brains for both doses of input inoculum. At no point does the recoverable viral titer rise above that of the input inoculum.

A possible explanation for this observation was that virus recovered from brains of mice inoculated with the vhs mutants represented input viral inoculum which had not been cleared from the brain, rather than representing a reduced level of viral replication.

To test this possibility, mice were inoculated with $5\times10^5$ pfu of the ICP27⁻ virus 5 d/1.2. Since this virus is replication deficient, one could accurately assess whether input replication-defective virus was recoverable or if it was cleared from the brain. At day three post-infection, the inventors found no recoverable 5 d/1.2 virus when brain homogenates were plated on the complementing 3—3 cell line, whereas control infections with KOS yielded $1\times10^4$ pfu/gram wet weight of wild-type virus. This result demonstrates that the level of virus recovered from brains represents a reduced level of replication rather than resulting from an inability of the virus to be cleared.

Figure 7A:
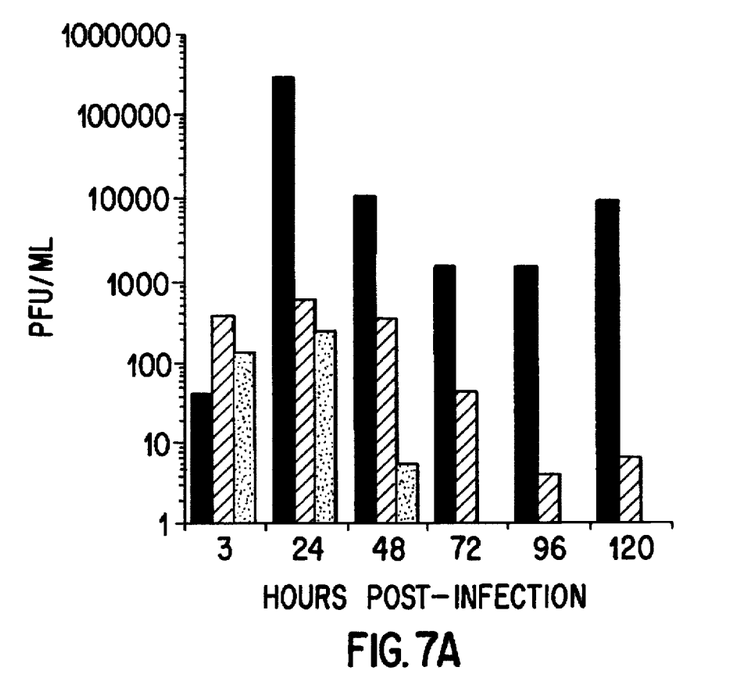
FIG. 7, in two parts, A and B, shows acute viral replication in mice. Logarithmic mean titers of KOS, vhs-ΔSma and UL41NHB in mice following corneal inoculation with $2\times10^6$ pfu/eye of virus.

Acute replication in the mouse eye was analyzed at 3, 24, 48, 72, 96 and 120 hours post-infection. These results are presented graphically in FIG. 7A. There were no time points taken for vhs-ΔSma past 72 hours. The replication of UL41NHB was reduced by 10- to 100-fold compared to KOS by 24 hours post-infection and the level of recoverable mutant virus remained decreased by at least 10-fold out to 120 hours post-infection. By 48 hours post-infection, the level of recoverable vhs-ΔSma was 1000-fold reduced from KOS. There was no detectable vhs-ΔSma at 72 hours post-infection. These results demonstrate a restriction to vhs mutant replication in peripheral tissues.

Figure 7B:
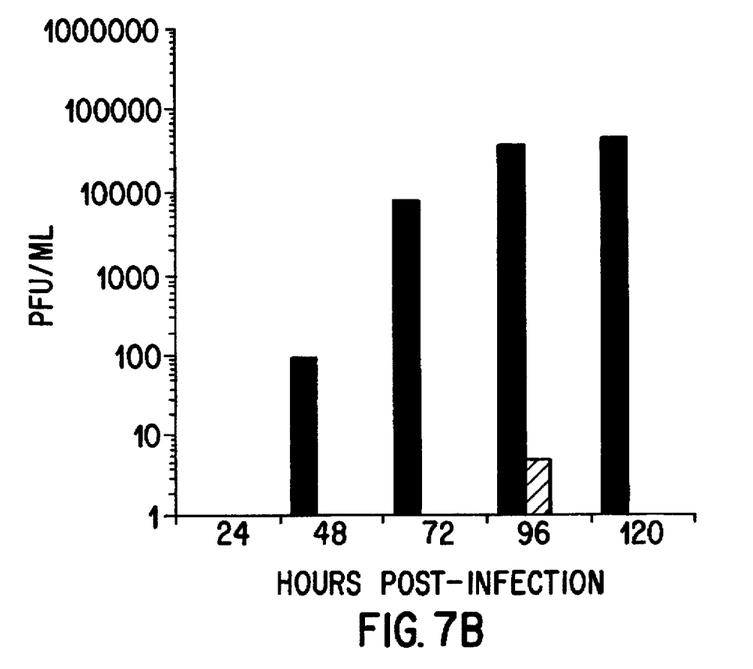

These mutants were severely restricted for replication at the level of the trigeminal ganglia (FIG. 7B). While KOS was readily detectable after 48 hours post-infection, infectious virus was never detected for vhs-ΔSma out to 120 hours post-infection. Only one (1) ganglion out of 20 infected with UL41NHB yielded detectable virus. This virus was not detected until 96 hours post-infection, and the level of virus recovered was decreased by more than 10,000-fold from KOS.

To ensure that the infectious virus recovered from the ganglion did represent UL41NHB and was not the result of contamination with KOS, the inventors performed a Southern blot analysis on viral DNA isolated from the infected trigeminal ganglion. The digestion pattern from this analysis was consistent with UL41NHB, demonstrating that UL41NHB was present at some low level in this trigeminal ganglion.

Explant cocultivation reactivation investigations.

The tests performed for this investigation were done using standard explant cocultivation assays with trigeminal ganglia being removed at 28 days post-infection. The results shown in Table 1, below, represent data from five independent tests for KOS, three independent tests for vhs-ΔSma and two independent tests for UL41NHB.

The reactivation frequency for KOS (44 of 62 ganglia, or 71%) was similar to previously published results (57). The in-frame deletion mutant vhs-ΔSma was not reactivation-competent by this assay (0 of 40 ganglia reactivated, or 0%). The illustrative truncation mutant, UL41NHB, reactivated in only 1 of 28 ganglia (4%). These results indicate that the vhs mutants are significantly reduced in their ability to reactivate from latency in the mouse eye model and that vhs may play a role in reactivation from explant culture.

TABLE 1

Acute viral replication and reactivation from latency for KOS, UL41NHB and vhs-ΔSma.

| VIRUS | DAY 3 MEAN VIRAL TITRES (PFU/ML) FOUND IN: | | REACTIVATION* |
|---|---|---|---|
| | EYE SWABS | GANGLIA | |
| KOS | $1.45 \times 10^3$ | $6.81 \times 10^3$ | 44/62 (71%) |
| UL41NHB | $4.47 \times 10^1$ | 0 | 1/28 (4%) |
| vhs-ΔSma | 0 | 0 | 0/40 (0%) |

*NUMBER OF GANGLIA YIELDING VIRUS PER NUMBER OF GANGLIA ASSAYED

1. Ace, C. I., T. A. McKee, J. M. Ryan, J. M. Cameron, and C. M. Preston. 1989. Construction and characterization of a herpes simplex virus type 1 mutant unable to transinduce immediate-early gene expression. J. Virol. 63: 2260–2269.
2. Becker, Y., E. Tavor, Y. Asher, C. Berkowitz, and M. Moyal. 1993. Effect of herpes siplex virus type-1 UL41 gene on the stability of mRNA from the cellular genes: β-actin, fibronectin, glucose transporter-1, and docking protein, and on virus intrapedtoneal pathogenicity to newborn mice. Virus genes 7: 133–143.
3. Berthomme, H., B. Jacquemont, and A. Epstein. 1993. The pseudorabies virus host-shutoff homolog gene: nucleotide sequence and comparison with alphaherpesvirus protein counterparts. Virology 193: 1028–1032.
4. Brown, T. 1994. Preparation and analysis of RNA, pp. 4.9.1–4.9.5. In Ausubel, F. M., R. Brent, R. E. Kingston, et al. (ed.), Current protocols in molecular biology, suppl. 17. Wiley-Interscience, New York.
5. Bolovan, C. A., N. M. Sawtell, and R. L. Thompson. 1994. ICP34.5 mutants of herpes simplex virus type 1 strain 17syn+ are attenuated for neurovirulence in mice and for replication in confluent primary mouse embryo cell cultures. J. Virol. 68: 48–55.
6. Chou, J., and B. Roizman, 1992. The $\gamma_1$ 34.5 gene of herpes simplex virus 1 precludes neuroblastoma cells from triggering total shutoff of protein synthesis characteristic of programmed cell death in neuronal cells. Proc. Natl. Acad. Sci. USA 89: 3266–3270.
7. Clements, G. B., and P. G. E. Kennedy. 1989. Modulation of herpes simplex virus (HSV) infection of cultured neuronal cells by nerve growth factor and antibody to HSV. Brain 112: 1277–1294.
8. Coen, D. M., A. F. Irmiere, J. G. Jacobson, and K. M. Kerns. 1989. Low levels of herpes simplex virus thymidine-thymidylate kinases are not limiting for sensitivity to certain antiviral drugs or for latency in a mouse model. Virol. 168: 221–231.
9. Coen, D. M., M. Kosz-Vnenchak, J. G. Jacobson, D. A. Leib, C. L. Bogard, P. A. Schaffer, K. L. Tyler, and D. M. Knipe. 1989. Thymidine-kinase negative herpes simplex virus mutants establish latency in mouse trigeminal ganglia but do not reactivate. Proc. Natl. Acad. Sci. USA 86: 4736–4740.
10. Coen, D. M. 1992. Quantitation of rare DNAs by PCR, pp. 15.3.1–15.3.8. In Ausubel, F. M., R. Brent, R. E. Kingston, et al. (ed.), Current protocols in molecular biology, suppl. 17. Wiley-Interscience, New York.
11. Davido, D. J. and D. A. Leib. Unpublished data.
12. DeLuca, N. A., and P. A. Schaffer.1987. Activities of herpes simplex virus type I (HSV-1) ICP4 genes specifying nonesnse peptides. Nucleic Acids Res. 15: 4491–4511.

13. Dix, R. D., R. R. McKendall, and J. R. Baringer. 1983. Comparative neurovirulence of herpes simplex type 1 strains after peripheral or intracerebral inoculation of BALB/c mice. Infection and Immunity 40: 103–112.
14. Everett, R. D., and M. L. Fenwick. 1990. Comparative DNA sequence analysis of the host shutoff genes of different strains of herpes simplex virus: type 2 strain HG52 encodes a truncated UL41 product. J. Gen. Virol. 71: 1387–1390.
15. Fenwick, M. L., and J. Clark. 1982. Early and delayed shut-off of host protein synthesis in cells infected with herpes simplex virus. J. Gen. Virol. 61: 121–125.
16. Fenwick, M. L., and J. Clark. 1983. The effects of cycloheximide on the accumulation and stability of functional α-mRNA in cells infected with herpes simplex virus. J. Gen. Virol. 64: 1955–1963.
17. Fenwick, M. L., and R. D. Everett. 1990. Inactivation of the shutoff gene (UL41) of herpes simplex virus types 1 and 2. J. Gen. Virol. 71: 2961–2967.
18. Fenwick, M. L., and R. D. Everett. 1990. Transfer of UL41, the gene controlling virion-associated host cell shutoff, between different strains of herpes simplex virus. J. Gen. Virol. 71: 411–418.
19. Fenwick, M. L., and M. M. McMenamin. 1984. Early virion-associated suppression of cellular protein synthesis by herpes simplex virus is accompanied by inactivation of mRNA. J. Gen. Virol. 65: 1225–1228.
20. Fenwick, M., L. S. Morse, and B. Roizman. 1979. Anatomy of herpes simplex virus DNA XI. Apparent clustering of functions effecting rapid inhibition of host DNA and protein synthesis. J. Virol. 29: 825–827.
21. Fenwick, M. L., and S. A. Owen. 1988. On the control of immediate early (α) mRNA survival in cells infected with herpes simplex virus. J. Gen. Virol. 69: 2869–2877.
22. Fenwick, M. L., and M. J. Walker. 1978. Supression of the synthesis of cellular macromolecules by herpes simplex virus. J. Gen. Virol. 41: 37–51.
23. Fort, Ph., L. Marty, M. Piechaczyk, S. El Sabrouty, Ch. Dani, Ph. Jeanteur, and J. M. Blanchard. 1985. Vadous rat adult tissues express only one major mRNA species from the glyceraldehyde-3-phosphate-dehydrogenase multigenic family. Nucleic Acids Res. 13: 1431–1442.
234. Frink, R. J., K. P. Anderson, and E. K. Wagner. 1981. Herpes simplex virus type 1 HindIII fragment L encodes spliced and complementary mRNA species. J. Virol. 39: 559–572.
25. Garcia-Blanco, M., and B. R. Cullen. 1991. Molecular basis of latency in pathogenic human viruses. Science 254: 815–820.
26. Goldstein, D. J., and S. K. Weller. 1988. An ICP6::lacZ insertional mutagen is used to demonstrate that the UL52 gene of herpes simplex virus type 1 is required for virus growth and DNA synthesis. J. Virol. 62: 2970–2977.
27. Gordon, Y. J., J. L. C. McKnight, J. M. Ostrove, E. Romanowski, and T. Araullo-Cruz. 1990. Host species and strain differences affect the ability of an HSV-1 ICP0 deletion mutant to establish latency and spontaneously reactivate in vivo. Virology 178: 469–477.
28. Harlow, E. and D. Lane. 1988. Antibodies: a laboratory manual. Cold Spring Harbor Laoratory Press, Cold Spring Harbor, N.Y.
29. Hill, T. M., J. R. Sadler, and J. L. Betz. 1985. Vidon component of HSV 1 (KOS) interferes with ready shutoff of host protein synthesis induced by HSV-2 (186). J. Virol. 56: 312–316.
30. Honess, R. W., and B. Roizman. 1973. Proteins specified by herpes simplex virus. XI. Identification and relative molar rates of synthesis of structural and nonstructural herpesvirus polypeptides in the infected cell. J. Virol. 12: 1347–1365.
31. Honess, R. W., and B. Roizman. 1974. Regulation of herpesvirus macromolecular synthesis. L Cascade regulation of the synthesis of three groups of viral proteins. J. Virol. 14: 8–19.
32. Honess, R. W., and B. Roizman. 1975. Regulation of herpesvirus macromolecular synthesis: sequential transition of polypeptide requires functional viral polypeptides. Proc. Natl. Acad. Sci. USA 72: 1276–1280.
33. Inglis, S. C. 1982. Inhibition of host protein synthesis and degradation of cellular mRNAs during infection by Influenza and herpes simplex virus. Mol. Cell. Biol. 2: 1644–1648.
34. Jacobson, J. G., D. A. Leib, D. J. Goldstein, C. L. Bogard, P. A. Schaffer, S. K. Weller, and D. M. Coen. 1989. A herpes simplex virus ribonucleotide reductase deletion mutant id defective for productive acute and reactivatable latent infections of mice and for replication in mouse cells. Virology 173: 276–283.
35. Katz, J. P., T. Bodin, and D. M. Coen. 1990. Quantitative polymerase chain reaction analysis of herpes simplex virus DNA in ganglia of mice infected with replication-incompetent mutants. J. Virol. 64: 4288–4295.
36. Krikorian, C. R., and G. S. Read. 1989. Proteins associated with mRNA in cells infected with herpes simplex virus. Biochem. and Biophys. Res. Comm. 164: 355–361.
37. Krikorian, C. R., and G. S. Read. 1991. In vitro mRNA degradation system to study the vidon host shutoff function of herpes simplex virus. J. Virol. 65: 112–122.
38. Kwong, A. D., and N. Frenkel. 1987. Herpes simplex virus-infected cells contain a function(s) that destabilizes both host and viral mRNAs. Proc. Natl. Acad. Sci. USA 84: 1926–1930.
39. Kwong, A. D., and N. Frenkel. 1989. The herpes simplex virus vidon host shutoff function. J. Virol. 63: 4834–4839.
40. Kwong, A. D., J. A. Kruper, and N. Frenkel. 1988. Herpes simplex virus virion host shutoff function. J. Virol. 62: 912–921.
41. Latchman, D. S., C. L. Dent, K. A. Lillycrop, and J. N. Wood. 1992. POU family transcription factors in sensory neurons. Biochemical Society Transactions 20: 627–631.
42. Leib, D. A., D. M. Coen, C. L. Bogard, K. A. Hicks, D, R. Yager, D. M. Knipe, K. L. Tyler, and P. A. Scaffer. 1989. Immediate-early regulatory gene mutants define different stages in the establishment and reactivation of herpes simplex virus latency. J. Virol. 63: 759–768.
43. Leib, D. A., K. C. Nadeau, S. A. Rundle, and P. A. Schaffer. 1991. The promoter of the latency-associated transcripts of herpes simplex virus type 1 contains a functional cAMP-response element: Role of the latency-associated transcripts and cAMP in reactivation of latency. Proc. Natl. Acad. Sci. (USA) 88: 48–52.
44. Lynas, C., T. J. Hill, N. J. Maitland and S. Love. 1993. Latent infection with the MS strain of herpes simplex type 2 in the mouse following intracerebral inoculation. J. of the Neurol. Sci. 120: 107–114.
45. MacLean, A. R., M. ul-Fareed, L. Robertson, J. Harland, and S. M. Brown. 1991. Herpes simplex virus type 1 deletion variants 1714 and 1716 pinpoint neurovirulence-related sequences in Glasgow strain 17+ between immediate early gene 1 and the 'a' sequence. J. Gen. Virol. 72: 631–639.
46. McCarthy, A. M., L. McMahan and P. A. Schaffer. 1989. Herpes simplex virus type 1 ICP27 deletion mutants exhibit altered patterns of transcription and are DNA deficient. J. Virol. 63: 18–27.

47. McGeogh, D. J., M. B. Dalrymple, A. J. Davison, A. Dolan, M. C. Frame, D. McNab, L. J. Perry, J. E. Scott, and P. Taylor. 1988. The complete DNA sequence of the long unique region in the genome of herpes simplex virus type 1. J. Gen. Virol. 69: 1531–1574.

48. McLauchlan, J.,C. Addison, M. C. Craigie, and F. J. Rixon. 1992. Noninfectious L-particles supply functions which can facilitate infection by HSV-1. Virology 190: 682–688.

49. Mitchell, W. J., R. J. De Santo, S-D Zhang, W. F. Odenwald, and H. Arnhelter 1993. Herpes simplex virus pathogenesis in transgenic mice is altered by the homeodomain protein Hox 1.3. J. Virol. 67: 4484–4491.

50. Nichol, P. F., J. Y. Chang, E. M. Johnson, Jr., and P. D. Olivo. 1994. Infection of sympathetic and sensory neurones with herpes simplex virus does not elicit a shut-off of cellular protein synthesis: implications for viral latency and herpes vectors. Neurobiology of Disease 1: 83–94.

51. Ninkina, N. N., G. E. M. Stevens, J. N. Wood, and W. D. Richardson, 1993. A novel Brn3-like POU transcription factor expressed in subsets of rat sensory and spinal cord neurons. Nucleic Acids. Res. 14: 3175–3182.

52. Nishioka, Y., and S. Silverstein. 1977. Degradation of cellular mRNA during infection by herpes simplex virus. Proc. Natl. Acad. Sci. USA 74: 2370–2374.

53. Nishioka, Y., and S. Silverstein. 1978. Alterations in the protein synthetic apparatus of friend erythroleukemia cells infected with vesicular stomatitis virus or herpes simplex virus. J. Virol. 25: 422–426.

54. Nishioka, Y., and S. Silverstein. 1978. Requirement of protein synthesis for the degradation of host mRNA in friend erythroleukemia cells infected with herpes simplex virus type 1. J. Virol. 27: 619–627.

55. Oroskar, A. A., and G. S. Read. 1987. A mutant of herpes simplex virus type 1 exhibits increased stability of immediate-early (alpha) mRNAs. J. Virol. 61: 604–606.

56. Oroskar, A. A., and G. S. Read. 1989. Control of mRNA stability by the virion host shutoff function of herpes simplex virus. J. Virol. 63: 1897–1906.

57. Rader, K. A., C, E. Ackland-Berglund, J. K. Miller, J, S. Pepose, and D. A. Leib. 1993. In vivo characterization of site-directed mutations in the promoter of the herpes simplex virus type 1 latency-associated transcripts. J. Gen. Virol. 74: 1859–1869.

58. Read, G. S., and N. Frenkel. 1983. Herpes simplex virus mutants defective in the virion-associated shutoff of host polypeptide synthesis and exhibiting abnormal synthesis of α (immediate early) viral polypeptides. J. Virol. 46: 498–512.

59. Read, G. S., B. M. Karr, and K. Knight. 1993. Isolation of a herpes simplex virus type 1 mutant with a deletion in the vidon host shutoff gene and identification of multiple forms of the vhs (UL41) polypeptide. J. Virol. 67: 7149–7160.

60. Roizman, B., G. S. Borman, and M-K. Rousta. 1966. Macromolecular synthesis in cells infected with herpes simplex virus. Nature 206: 1374–1375.

61. Roizman, B., and A. E. Sears. 1991. Herpes simplex virus viruses and their replication, pp. 849–895. In B. N. Fields and D. M. Knipe (ed.), Fundamental Virology, 2nd ed. Raven Press, Ltd., N.Y.

62. Sacks, W. R., C. C. Greene, D. P. Aschman, and P. A. Schaffer. 1985. Herpes simplex virus type 1 ICP27 is an essential regulatory protein. J. Virol. 55: 796–805.

63. Sambrook, J., E. F. Fritsch, and T. Maniatis. 1989. Molecular cloning: A laboratory manual, 2nd ed. Cold Spring Harbor Laboratory Press. Cold Spring Harbor, N.Y.

64. Schaffer, P. A., V. C. Carter and M. C. Timbury. 1978. Collaboration complementation study of temperature sensitive mutants of herpes simplex virus types 1 and 2. Virology. 27: 490–504.

65. Schek, N., and S. L. Bachenheimer. 1985. Degradation of cellular mRNAs induced by a virion-associated factor during herpes simplex virus infection of vero cells. J. Virol. 55: 601–610.

66. Shepard, A. A., A. N. Imbalzano, and N. A. DeLuca. 1989. Separation of primary structural components conferring autoregulation, transactivation, and DNA-binding properties to the herpes simplex virus transcriptional regulatory protein ICP4. J. Virol. 63: 3714–3728.

67. Silverstein, S., and D. L. Englehardt. 1979. Alterations in the protein synthetic apparatus of cells infected with herpes simplex virus. Virology. 95: 334–342.

68. Smibert, C. A., and J. R. Smiley. 1990. Differential regulation of endogenous and transduced β-globin genes during infection of erythroid cells with a herpes simplex virus type 1 recombinant. J. Virol. 64: 3882–3894.

69. Smibert, C. A., D. C. Johnson, and J. R. Smiley. 1992. Identification and characterization of the vidon-induced host shutoff product of herpes simplex virus gene UL41. J. Gen. Virol. 73: 467–470.

70. Smibert, C. A., B. Popova, P. Xiao, J. P. Capone, and J. R. Smiley. 1994. Herpes simplex virus VP16 forms a complex with the virion host shutoff protein vhs. J. Virol. 68: 2339–2346.

71. Smiley, J. R., C. Smibert, and R. D. Everett. 1987. Expression of a cellular gene cloned in herpes simplex virus: rabbit beta-globin is regulated as an early viral gene in infected fibroblasts. J. Virol. 61: 2368–2377.

72. Sorenson, C. A., P. A. Hart, and J. Ross. 1991. Analysis of herpes simplex virus-induced mRNA destabilizing activity using an in vitro mRNA decay system. Nucleic Acids Res. 19: 4459–4465.

73. Steiner, I., J. G. SPivack, S. L. Deshmane, C. I. Ace, C. M. Preston, and N. W. Fraser. 1990. A herpes simplex virus type 1 mutant containing a nontransinducing Vmw65 protein established latent infection in vivo in the absence of viral replication and reactivates efficiently from explanted trigeminal ganglia. J. Virol. 64: 1630–1638.

74. Strelow, L. I., and D. A. Leib. Unpublished data.

75. Strom, T., and N. Frenkel. 1987. Effects of herpes simplex virus on mRNA stability. J. Virol. 61: 2198–2207.

76. Sydiskis, R. J., and B. Roizman. 1966. Polysomes and protein synthesis in cells infected with a DNA virus. Science 153: 76–78.

77. Sydiskis, R. J., end B. Roizman. 1967. The disaggregation of host polyribosomes in productive and abortive infection with herpes simplex virus. Virology 32: 678–686.

78. Tenser, R. B., and M. E. Dunstan. 1979. Herpes simplex virus thymidine kinase expression in infection of the trigeminal ganglion. Virology. 99: 417–422.

79. Tenser, R. B., W. A. Edris, end K. A. Hay. 1993. Neuronal control of herpes simplex virus latency. Virology 195: 337–347.

80. Weinheimer, S. P., B. A. Boyd, S. K. Durham, J. L. Resnick, and D. R. O'Boyle. 1992. Deletion of the VP16 open reading frame of herpes simplex virus type 1. J. Virol. 66: 258–269.

81. Whitley, R. J., E. R. Kern, S. Chatterjee, J. Chou, and B. Roizman. 1993. Replication, establishment of latency, and induced reactivation of herpes simplex virus $_{\gamma_1}$ 34.5 deletion mutants in rodent models. J. Clin. Invest. 91: 2837–2843.

82. Wilcox, C. L., and E. M, Johnson. 1987. Nerve growth factor deprivation results in the reactivation of latent herpes simplex virus in vitro, J. Virol. 61: 2311–2315.
83. Yao, F., and R. J. Courtney. 1992. Association of ICP0 but not ICP27 with purified virions of herpes simplex virus type 1. J. Virol. 66: 2709–2716.

Various other examples will be apparent to the person skilled in the art after reading the present disclosure without departing from the spirit and scope of the invention. It is intended that all such other examples be included within the claims appended hereto.

What is claimed:

1. An isolated recombinant HSV mutant UL41NHB deficient in vhs-induced shutoff function and attenuated in CD-1 mice in its ability to replicate at the periphery and in the nervous system and in its ability to reactivate from latency.

* * * * *